(12) United States Patent
Mathew et al.

(10) Patent No.: US 9,731,108 B2
(45) Date of Patent: Aug. 15, 2017

(54) BIO-MEDICAL ELECTRODE PAD

(71) Applicant: KONINKLIJKE PHILIPS N.V., Eindhoven (NL)

(72) Inventors: Denny Mathew, Eindhoven (NL); Severin Luc Ramses Harvey, Amsterdam (NL); Marnix The, s'Hertogenbosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/021,763

(22) PCT Filed: Sep. 10, 2014

(86) PCT No.: PCT/EP2014/069262
§ 371 (c)(1),
(2) Date: Mar. 14, 2016

(87) PCT Pub. No.: WO2015/036420
PCT Pub. Date: Mar. 19, 2015

(65) Prior Publication Data
US 2016/0228691 A1    Aug. 11, 2016

(30) Foreign Application Priority Data
Sep. 16, 2013 (EP) .................................. 13184626

(51) Int. Cl.
*A61N 1/00* (2006.01)
*A61N 1/04* (2006.01)
(Continued)

(52) U.S. Cl.
CPC .......... *A61N 1/0456* (2013.01); *A61B 5/0478* (2013.01); *A61B 5/04085* (2013.01);
(Continued)

(58) Field of Classification Search
USPC ........................................... 607/56, 148-149
See application file for complete search history.

(56) References Cited

U.S. PATENT DOCUMENTS

| 5,622,168 A | 4/1997 | Keusch et al. |
| 2008/0177168 A1* | 7/2008 | Callahan ............ A61B 5/04085 600/382 |

(Continued)

FOREIGN PATENT DOCUMENTS

| JP | 2011072543 A | 4/2011 |
| WO | 0215974 A1 | 2/2002 |

(Continued)

OTHER PUBLICATIONS

Axelgaard Manufacturing Co., Ltd; "Better Results Through Better Technology"; Company Brochure, 16 Page Document, 2012.

*Primary Examiner* — Nicole F Johnson
*Assistant Examiner* — Nicole F. Lavert

(57) ABSTRACT

The present application relates to an electrode pad comprising at least one electrode with an electrode terminal. A contact member such as a hydrogel is disposed on said electrode terminal and covered by a retainer mesh. The electrode terminal may be, for example, a silver electrode disposed on a flexible foil, and the contact member may be disposed in the aperture of a backing layer. The retainer mesh is designed to allow for an electrical contact of the contact member to an object such as the body of a person while at the same time mechanically retaining the contact member. Moreover, the electrode pad may comprise an array of several electrodes disposed on a carrier, said carrier having a slit separating at least two neighboring electrodes.

12 Claims, 5 Drawing Sheets

(51) Int. Cl.
*A61B 5/0408* (2006.01)
*A61B 5/0478* (2006.01)
*A61B 5/053* (2006.01)

(52) U.S. Cl.
CPC ............ *A61B 5/0536* (2013.01); *A61N 1/048* (2013.01); *A61N 1/0476* (2013.01); *A61N 1/0496* (2013.01)

(56) References Cited

U.S. PATENT DOCUMENTS

| 2011/0082383 A1* | 4/2011 | Cory .................... A61B 5/0536 600/547 |
| 2012/0253162 A1 | 10/2012 | Jones |
| 2012/0330394 A1* | 12/2012 | Dar ....................... A61F 5/0102 607/149 |
| 2013/0066412 A1 | 3/2013 | Van Der Beek et al. |

FOREIGN PATENT DOCUMENTS

| WO | 2011135498 A1 | 11/2011 |
| WO | 2011151742 A1 | 12/2011 |
| WO | 2012038878 A2 | 3/2012 |
| WO | 2012078937 A1 | 6/2012 |

\* cited by examiner

BIO-MEDICAL ELECTRODE PAD

CROSS-REFERENCE TO PRIOR APPLICATIONS

This application is the U.S. National Phase application under 35 U.S.C. §371 of International Application No. PCT/EP2014/069262, filed on Sep. 10, 2014, which claims the benefit of European Patent Application No. 13184626.3, filed on Sep. 16, 2013. These applications are hereby incorporated by reference herein.

FIELD OF THE INVENTION

The invention relates to a bio-medical electrode pad and a method for electrically contacting a biological object such as the body of a person or an animal. Moreover, it relates to a method for manufacturing an electrode pad.

BACKGROUND OF THE INVENTION

An electrode pad for biomedical applications such as transcutaneous electrical nerve stimulation (tens) is known. In general, a proper operation of electrode pads requires a good electrical contact to the skin during usage. However, current known electrode pads have multiple disadvantages. Firstly, such electrode pads include a gel layer that touches the skin directly, which at times causes annoyance to the user due to sticky nature of the gel. Furthermore, such electrode pads are not intended to be used for multiple times. The gel layer typically deteriorates by constant removal and application to the skin surface and it may thus lead to either uneven distribution of the current from the electrode terminal to the skin surface or direct contact of the electrode surface to the skin. Direct contact of the electrode surface to the skin leads to hot spots at times, which is undesirable.

SUMMARY OF THE INVENTION

It would therefore be desirable to have means that allow for a reliable and good electrical contact of electrodes in biomedical applications, particularly in cases of long-term and/or repeated usage.

This object is addressed by a bio-medical electrode pad, also referred to as the electrode pad, according to claim 1. Preferred embodiments are disclosed in the dependent claims.

According to a first aspect, an embodiment of the invention relates to an electrode pad for electrically contacting a biological object, also referred to as the object, such as a human or animal body, said electrode pad comprising at least one electrode with the following components:
an electrode terminal;
a contact member that is disposed on the electrode terminal wherein the electrode terminal is brought into electrical contact with the biological object via the intermediate contact member;
a retainer mesh that covers the contact member, wherein, the retainer mesh comprises a plurality of openings and wherein the contact member is arranged to directly contact the biological object through the plurality of openings.

The term "electrode terminal" shall denote an electrically conductive unit, element or member to which electrical voltages and/or currents can be supplied by some external control circuit (which is usually no part of the electrode pad but reversibly connectable to it). The electrode terminal is typically rigid and not optimally suited for directly contacting a biological object.

The "contact member", on the contrary, shall be designed such that it can make a good and preferably long-term electrical contact to a biological object such as the skin of a person while at the same time having a good electrical contact to the electrode terminal. For this reason, the contact member will usually be electrically conductive and soft or flexible to allow for a tight alignment to the (irregular) surface of an object.

The feature that the contact member is disposed "on" the electrode terminal shall imply no restriction with respect to the spatial orientation of the electrode pad. For purposes of defining the construction of the electrode pad, this term just refers to some (arbitrary) reference orientation in which the electrode terminal is at the bottom below the contact member and the retainer mesh.

The contact member will usually be larger than the electrode terminal to ensure that the latter is completely covered and cannot directly contact an object. Additionally or alternatively, the retainer mesh is usually larger than the contact member to allow for a fixation of the mesh at other structures of the electrode than the contact member.

If the electrode pad comprises more than one electrode terminal, each of these terminals will usually have an associated contact member of its own.

According to a second aspect, an embodiment of the invention relates to a method for electrically contacting an object such as a human or animal body. The method comprises that an electrode terminal is brought into electrical contact with the object via an intermediate contact member, wherein said contact member is covered by a retainer mesh comprising a plurality of openings and wherein the contact member is arranged to directly contact the object through the plurality of openings.

This method comprises, in general form, the steps that can be executed when an electrode pad of the kind described above is applied. Explanations provided for the electrode pad are therefore analogously valid for this method and vice versa.

According to a third aspect, an embodiment of the invention relates to a method for manufacturing an electrode pad, said method comprising the following steps:
Disposing a contact member on an electrode terminal.
Covering said contact member with a retainer mesh comprising a plurality of openings for letting the contact member to directly contact the object.

The manufactured electrode pad may particularly be an electrode pad of the kind defined above. Explanations provided for the latter are therefore analogously valid for the manufacturing method and vice versa.

The above defined embodiments of the invention have the advantage that they allow for making a good mechanical and electrical contact to a biological object because the contact member serves as an interface between said object and the electrode terminal. Moreover, long-term functioning of this design is guaranteed by the usage of the retainer mesh that covers the contact member. The retainer mesh provides a proper attachment of the contact member to the electrode terminal and prevents sticking of the contact member to the biological object (during usage) and thus avoiding annoyance and also ease the application and removal on human or animal (biological object) that are often painful, while at the same time allowing electrical contact between the contact member and the biological object directly through a plurality of openings, also may be referred to as the mesh openings.

There are multiple advantages of the electrode pad as described above. Firstly, the annoyance as described above is reduced since the gel contacts the skin through the openings only. Secondly, since the gel is covered by retainer mesh, the frequent removal and application of the electrode pad does not deteriorate the lifetime of the electrode pad, thus also increasing the cost effectiveness. Also, since the retainer mesh avoids accidental removal and deterioration of the gel layer, hot spots are also avoided.

In the following, various preferred embodiments of the invention are described that can be realized in combination with the electrode pads and the methods described above.

In one preferred embodiment, the contact member comprises a material selected from the group consisting of a gel, which can absorb and retain significant amounts of water, particularly a hydrogel, most preferably a hydrogel made up of cross-linked polymer chains such as Polyethylene-Oxide, Polyvinylpyrrolidone or Polysaccharide Karaya. A hydrogel is particularly suited for providing a good mechanical and electrical contact to a biological object such as the skin of a person.

The electrode terminal is preferably disposed on some kind of carrier that provides mechanical support and typically constitutes a body of the electrode pad that can be handled by a user. The carrier is preferably electrically insulating to prevent an uncontrolled spreading of electrical signals from an electrode and to insulate electrodes from each other if several of them are disposed on the same carrier. The carrier may for example be or comprise a flexible foil such as a PET foil. The retainer mesh may be directly or indirectly attached to the carrier, thus fixing the contact member to the carrier, too.

In another embodiment, the electrode pad comprises a "backing layer" having an aperture in which the contact member is accommodated. The backing layer may be identical to the aforementioned carrier or be a separate component of its own. Preferably, both a backing layer and a carrier are provided, wherein the backing layer is directly or indirectly attached to the carrier. With its aperture, the backing layer provides a stable accommodation for the—typically soft—contact member.

In a further development of the aforementioned embodiment, the retraining mesh is attached to the backing layer.

In a preferred design that combines some of the above features, the contact member is securely held in place by the aperture of a backing layer and by the electrode terminal (and/or by the carrier on which the electrode terminal is disposed, if present) on all sides that are not intended to make contact to an object. On the top side of the contact member, which has to remain open for contacting an object, the mesh is provided that mechanically retains the contact member in the aperture while still allowing for an electrical contact through the mesh openings. Preferably the mesh completely covers said top side of the contact member and is fixed all around the aperture to the backing layer.

The dimensions of the retainer mesh have to be chosen appropriately in view of the intended application in order to achieve an optimal compromise between the mechanical retention of the contact member and a minimal interference with the electrical contacting of an object. In view of this, it is preferred that the openings of the retainer mesh have a diameter ranging between about 5 mm and about 0.05 mm, preferably between about 1.5 mm and about 0.5 mm. In this context, the diameter of a general, noncircular mesh opening may be defined as the diameter of the largest circle that completely fits into the opening. Further, the spacing (d) between each of the plurality of the openings may range between about 500 µm and about 25 µm, preferably between about 200 µm and about 50 µm.

Additionally or alternatively, the thickness of the retainer mesh may range between about 500 µm and about 25 µm, preferably between about 200 µm and about 50 µm.

The retainer mesh will preferably be electrically insulating to prevent an uncontrolled spreading of electrical signals.

The retainer mesh preferably comprises a material selected from the group consisting of polyethylene, polyester and polypropylene.

The electrode terminal may optionally comprise a metal, carbon, or metal or carbon filled polymers. Preferably, the top layer of the electrode terminal consists of an inert metal such as silver or its chloride.

In a further embodiment, the retainer mesh may be covered by an outer layer of an additional material in regions off (outside) the contact member. The material of this outer layer may particularly be chosen to have favorite properties with respect to the contacting of a biological object. It may for example be skin-friendly to allow for a long-term application to a person's skin.

The electrode pad may comprise just a single electrode. In a preferred embodiment, the electrode pad comprises however a plurality of electrodes that can independently be connected to and/or controlled by an external circuit. Most preferably, there are several electrodes with electrode terminals and associated contact members that are designed in the manner defined above, i.e. with the contact member being disposed on the electrode terminal and being covered by a retainer mesh.

In the aforementioned embodiment, each electrode terminal with associated contact member may be covered by an individual retainer mesh of its own. Preferably there is however at least one retainer mesh that covers several contact members. Most preferably, all contact members of the electrode pad are covered by this single (large) retainer mesh.

According to a fourth aspect, an embodiment of the invention relates to an electrode pad for electrically contacting an object such as a human or animal body, said electrode pad comprising a carrier with an array of electrodes on it, wherein the carrier has at least one slit running between at least two neighboring electrodes of the array.

As usual, the term "electrode" shall denote a unit or component via which electrical signals such as voltages or currents can be exchanged between some technical equipment and an object, e.g. a human or animal body. In a simple case, the "electrode" may just be a piece of material (e.g. metal). Typically, an electrode will however have a more elaborate structure comprising for example elements of different materials such as a metallic electrode terminal and a soft contact member. The electrode pad according to the fourth aspect may particularly be combined with an embodiment of the electrode pad of the first aspect (having an electrode with an electrode terminal, a contact member, and a retainer mesh).

Preferably, the electrodes of the electrode pad are independently controllable and electrically insulated from each other. Moreover, the electrodes are usually connected via lines or wires to some connection region on the carrier where they can centrally be contacted by external circuitry.

The "slit" in the carrier may be like a cut, i.e. having zero width such that opposite sides of the slit contact each other in the relaxed state of the electrode pad (i.e. when no tension or stress is exerted on the pad, for example when the pad lies loosely on a flat surface). It is however also comprised by the invention that opposite sides of the slit are separated by a gap of nonzero width (in the relaxed state of the electrode pad). The width of such a slit is typically smaller than about 20 mm, preferably smaller than about 10 mm, most preferably smaller than about 5 mm. If the width of the slit is not zero, it is typically larger than about 0.5 mm, preferably larger than about 1 mm.

The electrodes of the electrode pad are usually surrounded by carrier material. Typically, a strip of at least about 5 mm of carrier material is provided around an electrode. This material can for example be used to fix a retainer mesh that covers the electrode.

The described electrode pad has the advantage that, due to its slit, it can be fitted to objects of different size, for example to knees of different individuals. Moreover, when being attached to one object, the electrode pad provides for a better and more reliable contact of the electrodes because movements and changes of the shape of the object will not affect the attachment of electrodes as they are mechanically decoupled by the slit.

In the following, various preferred embodiments of the invention are described that can be realized in combination with the electrode pads and the methods according to all aspects of the invention described above.

Preferably, the electrodes of the electrode pad are distributed with a substantially even spatial density. A particularly preferred embodiment is one in which the distance between any neighboring electrodes that are separated by the slit is less than about 200% of the mean distance of neighboring electrodes of the array that are not separated by the slit. In this context, the "distance" between two (extended) electrodes shall measure their interspace, i.e. it may be defined as the smallest distance an arbitrary first point on the first electrode and an arbitrary second point on the second electrode can assume. Moreover, it goes without saying that all statements about the distribution of electrodes, their distance, etc. refer to the relaxed state of the electrode pad if not indicated otherwise.

In general it is possible that the electrodes of the electrode pad have some irregular arrangement, for example a random distribution or a distribution corresponding to some irregular individual pattern. In a preferred embodiment, the electrodes of the array are arranged in a grid pattern, i.e. lined up in a pattern of (curved and/or straight) "rows" and "columns". The grid may particularly have a regular appearance with even distances between all rows and/or even distances between all columns, though an irregular pattern with varying distances between rows and/or columns is possible, too. Furthermore, the outer shape of the grid may be rectangular (with all rows/columns having the same number of electrodes) or not (having at least two rows/columns with different numbers of electrodes).

The slit may completely lie in the interior of the carrier. In a preferred embodiment, the slit starts (or ends) however at the border of the carrier, thus allowing for a maximal flexibility of the electrode arrangement.

The electrode pad may preferably have a symmetrical shape. If the slit does not coincide with the axis of symmetry, such a symmetrical shape implies that there are at least two slits of symmetrical arrangement. It should be noted, however, that asymmetric shapes of the electrode pad are possible, too, for example if the electrode pad is adapted to a specific body site (e.g. left knee).

The carrier on which the array of electrodes is disposed is preferably flexible, thus allowing for an alignment of the electrode pad to the usually irregular three dimensional surface of an object. The flexibility of the carrier usually comprises that it can be bent. Additionally or alternatively, the carrier may be stretchable.

In another preferred embodiment, the electrode pad is designed for an application at a joint of a human or animal body, particularly for an application at a human knee. A joint is generally an object undergoing frequent and substantial changes of its three dimensional geometry, thus posing a high demand on the attachment of electrodes. By mechanically decoupling neighboring electrodes with a slit, the described electrode pad is optimally suited to fulfill these demands.

In various embodiments of the invention, the bio-medical electrode pad is attached to the biological object with the help of a strap. For instance, the electrode pad can be accommodated in the strap and then the strap can be used to fix around the biological site of the human or animal body with the help of Velcro®/mechanical hooks.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Figure 1:
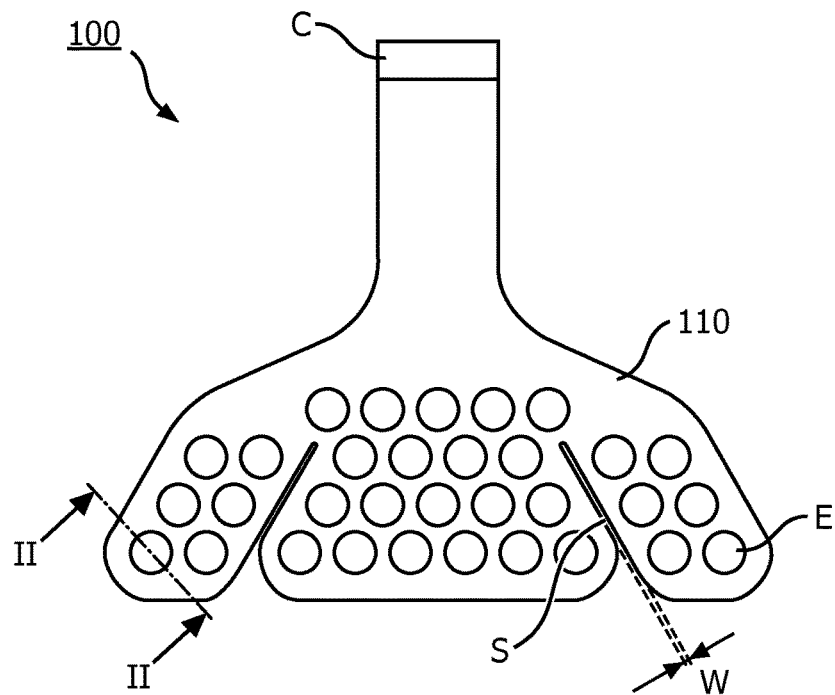
FIG. 1 shows a top view onto a first electrode pad according to an embodiment of the invention.

In the following, embodiments of the present invention will be illustrated with respect to an application in transcutaneous electrical nerve stimulation (TENS), though the approach is analogously applicable in many other areas, too, such as functional electrical stimulation (FES), electrocardiography (ECG), electroencephalography (EEG) or electrical impedance tomography (EIT).

TENS is the use of electric current produced by a device to stimulate nerves for therapeutic purposes. One main application of these TENS devices is pain relief. The theory is that a TENS device generates electrical current pulses that excite specific nerves (so-called Aβ nerves), that causes an inhibition of the signals through other nerves coming from the tissue damage location. In this way, chronic pain can be suppressed to certain extend.

In one type of TENS, the stimulation signal may be applied to the skin using a pair of large electrodes (e.g. squares of 4×4 $cm^2$ or 5×5 $cm^2$, or circles with 4-5 cm diameter). The patient knows where to place the electrodes on the body from the Instructions for Use delivered with the device or from recommendations of a General Practitioner or a Physiotherapist.

In another type of TENS, the device itself may be able to find the right nerve location for the stimulation. The electrodes of such a device should be significantly smaller (typical diameter about 1 cm), and a multitude of electrodes has to be connected to the skin. Electrical impedance may be measured on all electrodes. The electrode with the lowest impedance (the "stimulation electrode") may then be connected to one polarity of the stimulation means, while a multitude of other electrodes are connected to the other polarity ("common"). Stimulation can be done on more than one electrode at the same time, or on electrodes in different regions of the assembly of electrodes, but the common will always be a multitude of electrodes.

Irrespective of the type of TENS device, it is important to have a proper skin contact of the electrodes during the whole period of stimulation. It is practically more difficult to achieve this in targeted stimulation TENS devices as there many small electrodes. Therefore, generally, these electrode arrays need to be fixated to the location of the skin (e.g. knee for osteoarthritis patients) by an extra means such as a brace to wrap around the electrode.

To enhance the skin contact and comfort, carbon, silver or silver chloride electrodes may be used in combination with liquid or solid hydrogel as a medium between the skin and electrode (the size of the gel preferably being slightly larger than the size of the electrode to prevent the current density distribution issues during stimulation). However, when these electrode pads are worn for a few hours, hydrogel absorbs water from the sweat, which reduces the adhesion between the hydrogel dots and silver electrodes. Additionally, the skin and muscle movements during the activities cause the electrode pad to move over the skin, which induces stress and strain on the hydrogel dots. Both effects can result in lifting off the hydrogel edges. When worn continuously, these lifted hydrogel dots may roll up and eventually peel off from the electrodes. Shear forces between the brace and the skin might accelerate the edge lifting and peeling off the gel from the electrode positions. This results in a risk of having carbon or silver electrodes directly in contact with the skin during stimulation and restricts the long term usage of the electrode pad and lead to unpleasant stimulation sensations.

While it is possible to use disposable hydrogel electrodes only one times, a method is proposed here of building an electrode array based on hydrogels which can be re-used for long duration. According to this approach, it is suggested to use a mesh as mechanical reinforcement to hold the hydrogel to the electrode pad backing.

Moreover, size variations between different objects are both an economic and a technical issue. For example, not all knees have the same shape and not all legs have the same size yet it would be economical to have to provide just one type of electrode pad. In another, independent aspect, it is therefore proposed to introduce at least one slit into the electrode pad, thus improving the fit on different knee geometries and making it possible to produce only one electrode size.

FIG. 1 shows a top view of an electrode pad 100 according to an exemplary embodiment of the aforementioned proposals. The electrode pad 100 has a support structure comprising a carrier layer 110 that is for example appropriately shaped with respect to an application to the knee of a person. The electrode pad further comprises an array with (here 32 circular) stimulation electrodes E. Electrical lines (not shown) lead from these electrodes to a connector C for the individual electrical connection of each stimulation electrode to an external control circuit (not shown).

The 32 electrodes of the array are arranged in a grid pattern with four straight (horizontal) rows having 5, 8, 9, and 10 electrodes, respectively. The electrodes are further lined up in (slanted) columns. Furthermore, two slits S are provided in the carrier 110 that are arranged symmetrically (with respect to the symmetry axis of the electrode pad 100) and that cut through the bottom three rows. These slits S separate neighboring electrodes in these rows, thus decoupling them mechanically. The width w of the slits typically ranges between about 0.5 mm and 5 mm.

Figure 2:
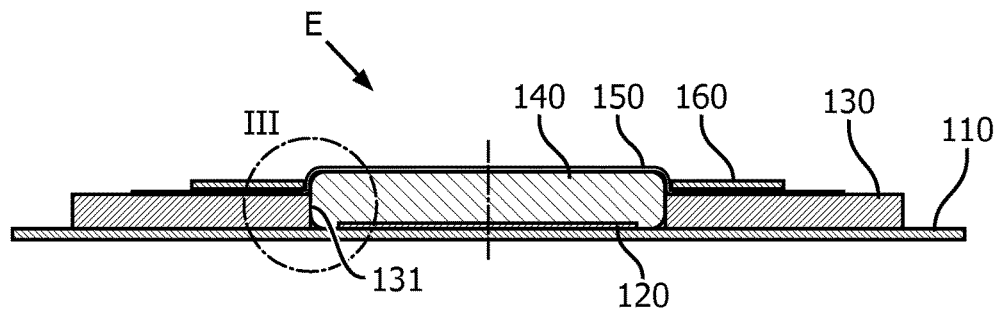
FIG. 2 shows a section through the first electrode pad along line II-II of FIG. 1.
Figure 3:
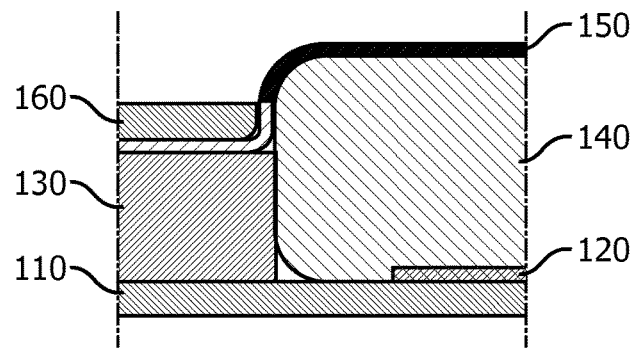
FIG. 3 shows an enlarged detail III of FIG. 2.

FIGS. 2 and 3 show in a section along line II-II of FIG. 1 in more detail the layered structure at a stimulation electrode E. From bottom to top, the simulation electrode E and its surrounding comprise the following stack of layers and materials:

A large carrier 110 that provides support for the stimulation electrode and connection of the whole electrode pad. The carrier may for example consist of polyethylene terephthalate (PET), or polyimide (PI) foil.

An electrode terminal 120 that is printed onto the carrier 110. The electrode terminal 120 is electrically connected to external circuits via lines running on top of the carrier 110 that are not shown in detail. It may for example consist of silver.

A "backing layer" 130 that is disposed on top of the carrier 110 and that provides an aperture 131 around the electrode terminal 120. The backing layer may for example consist of polyurethane (PU) foam, non-woven polyester fabric, and/or polyethylene terephthalate (PET).

A "contact member", here in the form of a piece of hydrogel 140 that is disposed on the electrode terminal 120 and fills the aperture 131 in the backing layer 130, extending horizontally (with respect to the drawing) beyond the electrode terminal 120 and vertically above the height of the backing layer 130.

Figure 4:
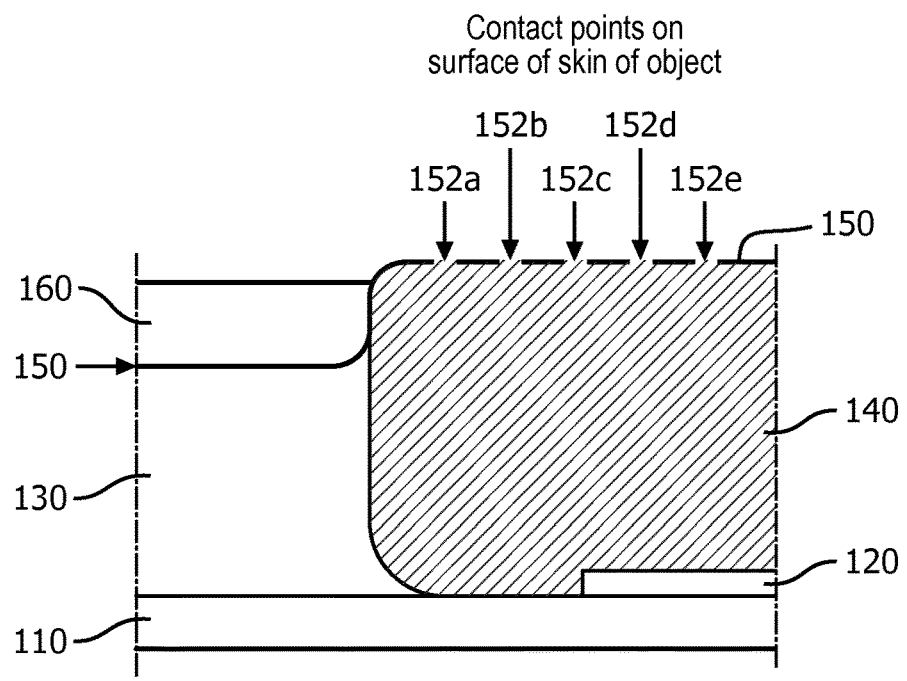
FIG. 4 shows a section through the electrode pad in use with an object/body.
Figure 5:
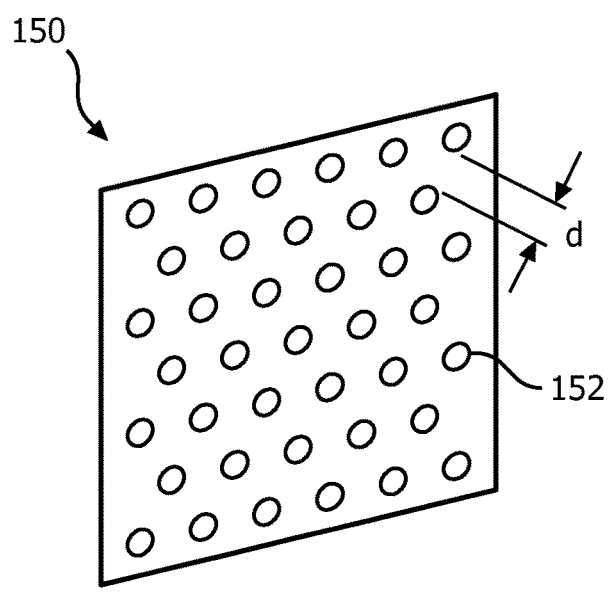
FIG. 5 shows a retainer mesh, according to an embodiment of the invention.

A net or mesh 150 ("retainer mesh") that completely covers the top side of the hydrogel 140 and that extends beyond the aperture 131, where it is glued, bonded, or otherwise fixed to the backing layer 130. The mesh 150 may for example comprise at least one of the following materials: polyethylene, polypropylene, and/or polyester. To further elaborate, the hydrogel 140 contacts the object/skin of the object through a plurality of openings 152, such as opening 152a-152e (FIG. 4). Further, the points, positions where the hydrogel 150 touches the skin of the object are called contact points. These contact points on the skin of the biological object receive the electrical stimulations from the electrode pad 100. The net/mesh 150 has plurality of openings that are structured closely to each other (FIG. 5). In an embodiment of the invention, the spacing (d) between the openings may range between about 500 µm and about 25 µm, preferably between about 200 µm and 50 µm.

The dimensions of the retainer mesh have to be chosen appropriately in view of the intended application in order to achieve an optimal compromise between the mechanical retention of the contact member and a minimal interference with the electrical contacting of an object. In view of this, it is preferred that the openings of the retainer mesh have a diameter ranging between about 5 mm and about 0.05 mm, preferably between about 1.5 mm and about 0.5 mm. In this context, the diameter of a general, noncircular mesh opening may be defined as the diameter of the largest circle that completely fits into the opening.

An additional (optional) outer layer 160 that covers the mesh 150 in regions above the backing layer 130, i.e. off the aperture 131 with the hydrogel 140. The outer layer may for example be made from skin-friendly material such as (e.g. PU) foam or a felt.

The mesh or net like structure 150 makes the hydrogel 140 resistant to skin movements during activities as well as when the adhesion drops during sweat build up.

Preferably, the mesh layer 150 extends beyond the position of a single electrode and spreads over all electrodes of the electrode pad 100, but without causing any electrical short circuit between the electrodes. The mesh is hence usually non-conductive. Most importantly, the mesh does not prevent or inhibit the skin contact or comfort of the hydrogel 140.

In experiments with the described design, lifetime testing and user testing was performed and showed that the addition of the mesh prevents the hydrogel from detaching from the electrode pad.

An exemplary method of manufacturing the described electrode pad 100 may comprise the following steps:

Printing silver pads onto a flex foil (110) to produce the electrode terminals 120. Additionally, a wire pattern may be printed onto the foil with conductive ink (e.g. silver, carbon). Where necessary the conductive ink is insulated with flexible dielectric paint or foil. Moreover, at least one slit may be cut into the foil.

Applying a pre-cut foam to the flex foil to produce the backing layer 130.

Applying hydrogel 140 on the silver pads.

Applying a mesh 150 over the hydrogel.

Applying a pre-cut skin-friendly layer 160.

Sealing the whole device in a bag for transportation.

After applying the hydrogel 140 onto the electrode terminals 120, a mesh/net like structure is applied on top of the hydrogel. This mesh can be laminated to the backing layer (pre-cut foam). The thickness and the plurality of the openings of the mesh should be chosen in such a way that the hydrogel must make skin contact, but should not cause any gel to be sheared off through the openings.

In summary, an embodiment according to one aspect of the invention has been described in which a contact member such as a hydrogel 140 is disposed on an electrode terminal 120 of an electrode pad 100. The delamination of hydrogel, a critical failure mode preventing the long time usage, can be minimized/eliminated by mechanically reinforcing the hydrogel to the electrode pad backing with a retainer mesh 150 or net like structure, without inhibiting the skin contact for sensing and actuation. In a preferred embodiment, the electrode terminal may for example be a silver electrode terminal 120 disposed on a flexible foil 110, and the contact member 140 may be disposed in the aperture 131 of a backing layer 130. The retainer mesh 150 is designed to allow for an electrical contact of the contact member 140 to an object such as the body of a person while at the same time mechanically retaining the contact member 140. The electrode pad provides for a long-lasting hydrogel based multi-array which can be used for multiple times.

Next, the aspect of the slits S in the electrode pad will be discussed in more detail.

Figure 6:
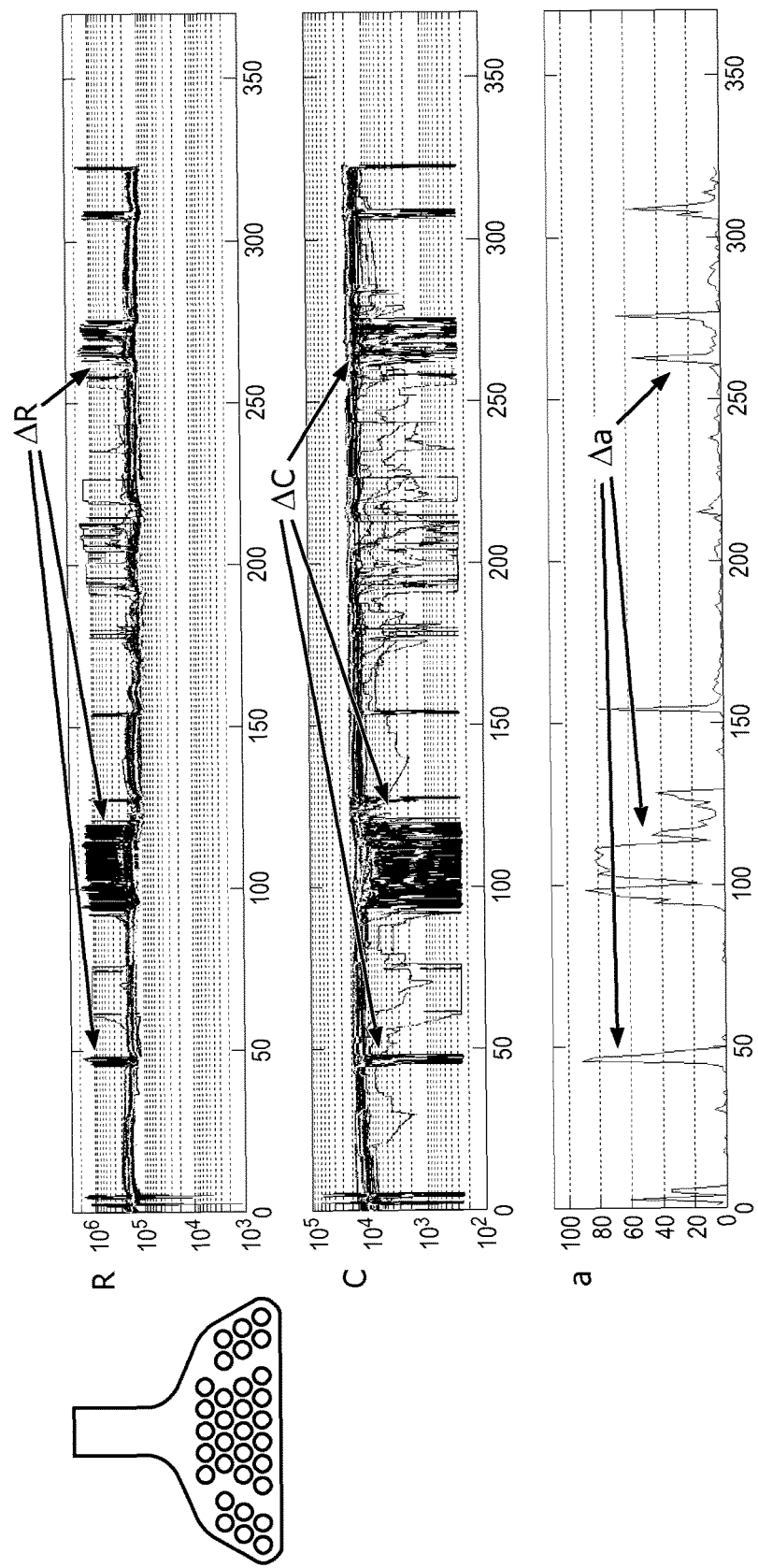
FIG. 6 shows measurements of electrical contact properties for an electrode pad without slits applied to a knee.

FIG. 6 shows diagrams of a typical measurement with a targeted stimulating device having no slits. As indicated to the left of the diagrams, the tested electrode pad contained 32 electrodes which measure skin resistance R (top diagram) and capacitance C (middle diagram). Also contained is an activity monitor which measures the user's activity "a" (bottom diagram). When the user was active one can clearly see that the electrode resistance R increases and the capacitance C decreases. The change in resistance, ΔR, and capacitance, ΔC, is rapid which is characteristic of the electrode becoming detached from the skin. This type of noise leads to erroneous measurements and can affect the stimulation sensation experienced by the user and should therefore be limited as much as possible.

Figure 7:
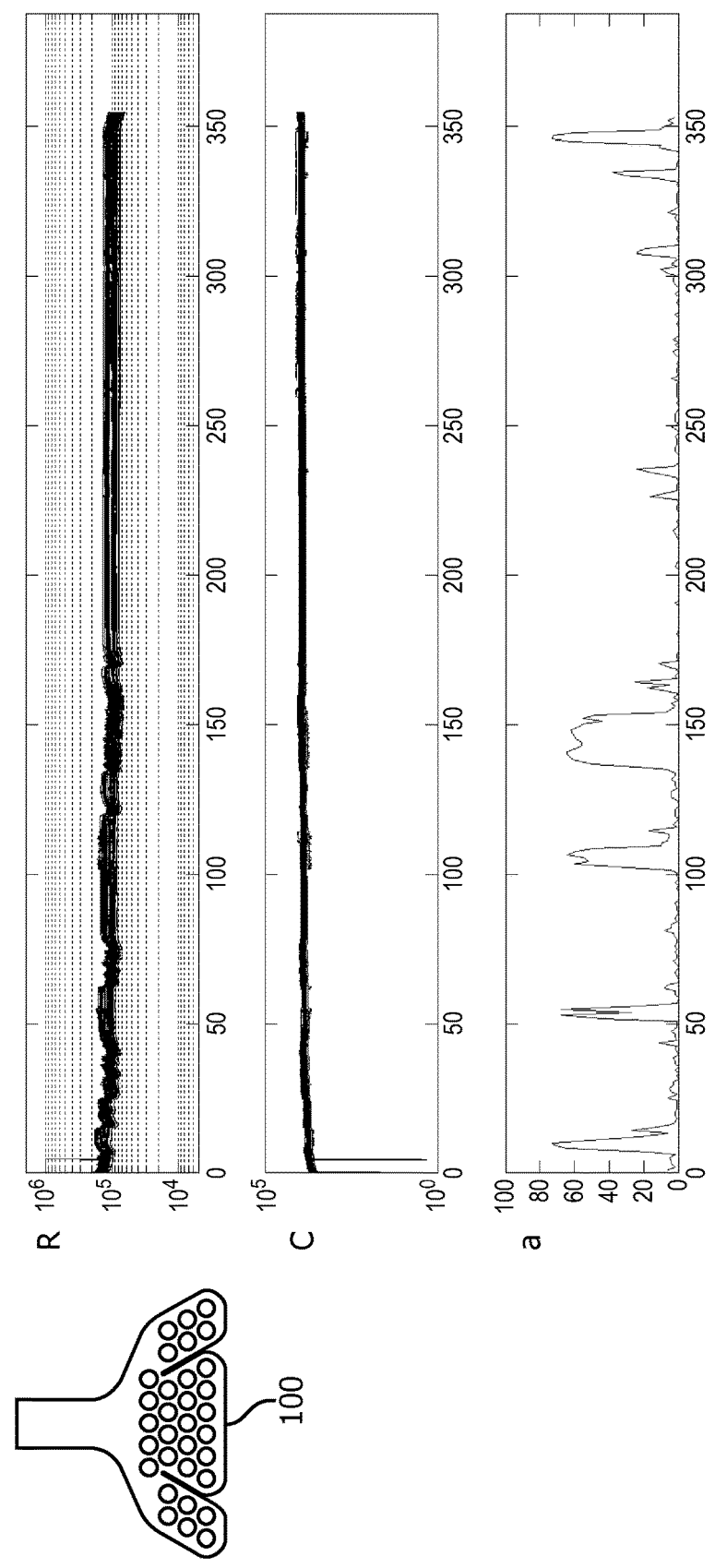
FIG. 7 shows comparable measurements for the first electrode pad.

FIG. 7 shows the impact of adding slits to the measurement of skin resistance R and capacitance C. Diagrams corresponding to those of FIG. 4 were measured, but now with an electrode pad 100 having slits as described above. One can clearly see that the measured signal is uniform and noise free even when activity increases. When this result is compared the one shown in FIG. 4 it is clear to see that the slits have greatly improved the ability of the electrode pad to measure skin impedance and deliver a continuous stimulation.

Figure 8:
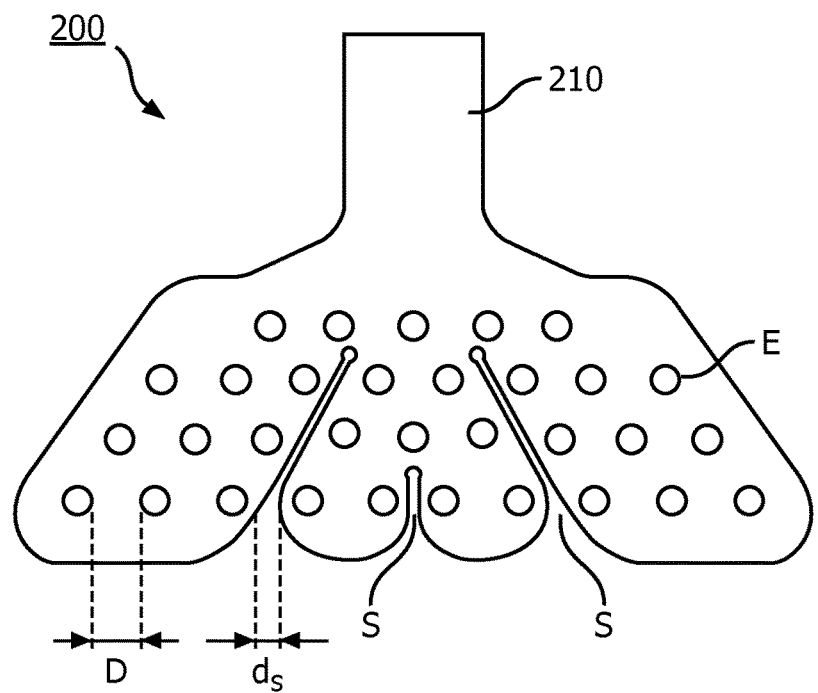
FIG. 8 shows a second electrode pad comprising three slits.

FIG. 8 shows a second embodiment of an electrode pad 200. In this pad, the carrier 210 with the array of electrodes E is structured by three symmetrically arranged slits S. Moreover, the interspace distance D between two neighboring electrodes that are not separated by a slit as well as the interspace distance $d_S$ between two neighboring electrodes that are separated by a slit is indicated. Preferably, the latter distance $d_S$ is less than about double the "normal" distance, i.e. $d_S \leq 2 \cdot D$, most preferably $d_S \leq 3/2 \cdot D$.

Figure 9:
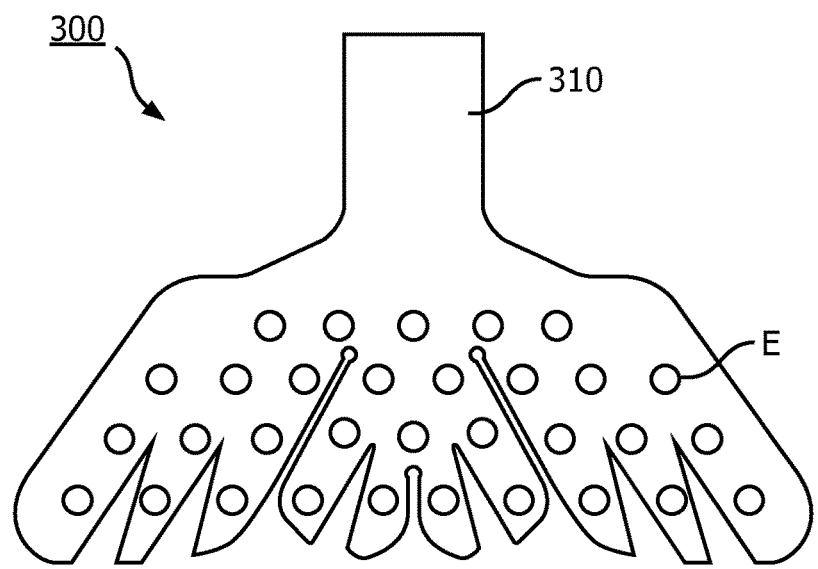
FIG. 9 shows a third electrode pad comprising nine slits.

FIG. 9 shows a third embodiment of an electrode pad 300 that comprises nine symmetrically arranged slits S.

The described electrode pads help to overcome three key issues:
 1. To fit all knee sizes and shapes.
 2. To be able to follow and conform to knee movements.
 3. Being comfortable and not limiting patient mobility. This is particularly important when the electrode pad needs to be worn for prolonged periods of time day after day. It therefore needs to be flexible and forgiving such that it does not lead to discomfort or prevent the user from being active.

In summary, an embodiment according to an aspect of the invention has been described in which an electrode pad comprises a carrier with an array of electrodes, wherein there is at least one slit in the carrier that runs between at least two neighboring electrodes of the array. Thus a multi electrode pad can be achieved which is flexible and conforming so as to ensure continuous electrical contact with the skin as well as a good fit on most knee geometries. The electrode pad is preferably designed out of flexible material which is slit in places so as to provide added flexibility.

The described embodiments can be used in any application where a long-lasting electrode pad is required for sensing or actuation on skin. Some specific examples are:

Transcutaneous electrical nerve stimulation (TENS), particularly knee pain stimulation;
general in-body sensing and actuation;
bio-impedance monitoring;
Electrical Impedance Tomography (EIT);
Functional Nerve Stimulation (FNS);
Functional Electrical Stimulation (FES).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A bio-medical electrode pad for electrically contacting a biological object, the electrode pad comprising at least one electrode with:
a carrier configured to support the electrode;
a backing layer disposed on the carrier, said backing layer having a plurality of apertures, each aperture having an electrode terminal and a gel contact member that is disposed on the electrode terminal wherein the electrode terminal is configured to be brought into electrical contact with the biological object via the intermediate gel contact member;
wherein each aperture is covered by a non-conductive retainer mesh material disposed on the gel contact member, wherein the retainer mesh material comprises a plurality of openings and wherein the gel contact member is arranged to directly contact the biological object through the plurality of openings.

2. The electrode pad according to claim 1, wherein the gel contact member comprises a material selected from the group consisting polyethylene-Oxide, polyvinylpyrrolidone or polysaccharide Karaya.

3. The electrode pad according to claim 1, wherein the carrier comprises a flexible foil.

4. The electrode pad, according to claim 1, wherein the retainer mesh material is attached to the backing layer.

5. The electrode pad according to claim 1, wherein the plurality of openings of the retainer mesh material have a diameter ranging between about 5 mm and about 0.05 mm.

6. The electrode pad according to claim 1, wherein the retainer mesh material has a thickness ranging between about 500 um and about 25 um.

7. The electrode pad according to claim 1, wherein the retainer mesh material comprises a material selected from the group consisting of polyethylene, polyester and polypropylene.

8. The electrode pad according to claim 1, wherein the electrode terminal comprises a metal selected from the group consisting of silver, carbon, and a polymer.

9. The electrode pad according to claim 1, wherein an outer layer is disposed on the backing layer in regions off each contact member.

10. The electrode pad according to claim 1, wherein a retainer mesh covers several contact members.

11. The electrode pad according to claim 1, wherein said carrier has at least one slit running between at least two neighboring apertures.

12. The electrode pad according to claim 1 wherein the spacing between the plurality of the openings is about 500 um and about 25 um.

* * * * *